United States Patent [19]

Ichinose et al.

[11] 4,045,764

[45] Aug. 30, 1977

[54] GAS-SENSING MATERIAL

[75] Inventors: Noboru Ichinose, Yokohama; Yuji Yokomizo, Tokyo; Masaki Katsura, Mitaka, all of Japan

[73] Assignee: Tokyo Shibaura Electric Co., Ltd., Tokyo, Japan

[21] Appl. No.: 621,575

[22] Filed: Oct. 10, 1975

[30] Foreign Application Priority Data

Oct. 15, 1974 Japan .............................. 49-117715
Feb. 13, 1975 Japan .............................. 50-17419

[51] Int. Cl.² ............................................. H01L 7/00
[52] U.S. Cl. ................................... 338/34; 252/518; 252/521
[58] Field of Search ................ 338/34, 35; 73/23, 27; 340/237; 23/232 E, 254 E, 255 E; 252/518, 521

[56] References Cited

U.S. PATENT DOCUMENTS

| 3,056,935 | 10/1962 | Jensen ................................. 338/35 |
| 3,903,226 | 9/1975 | Iga ..................................... 252/518 X |
| 3,926,858 | 12/1975 | Ichinose ............................ 252/521 X |

Primary Examiner—C. L. Albritton
Attorney, Agent, or Firm—Oblon, Fisher, Spivak, McClelland & Maier

[57] ABSTRACT

A gas-sensing material for detecting the presence particularly of hydrocarbon gases which is characterized by being formed of a sinter containing 20 to 99.85 mol % of ZnO, 0.1 to 50 mol % of MgO and 0.05 to 30 mol % of $Me_2O_3$ (Me denotes at least one element selected from the group consisting of gallium (Ga), boron (B), indium (In), iron (Fe), aluminium (Al) and chromium (Cr)), or another sinter prepared by blending 0.01 to 10% by weight of platinum (Pt) to the above-mentioned composition.

8 Claims, 7 Drawing Figures

GAS-SENSING MATERIAL

This invention relates to a gas-sensing material used in detecting the presence particularly of hydrocarbon gases.

A gas-sensing material is used in detecting gases from the electric resistance of said material which changes according to adsorption of gases to said material or desorption of gases therefrom with said electric resistance changes read out from a gas-sensing apparatus to determine the presence of gases. A gas-sensing material known to date is mainly composed of $SnO_2$. Among the prior art $SnO_2$ type gas-sensing materials, however, that which indicates linear electric resistance changes with respect to various gas concentrations has the drawback that said changes are too small for the gas-sensing apparatus to produce a sufficiently large output. On the other hand, conventional gas-sensing materials which are known to indicate noticeable electric resistance changes have a low degree of linearity, namely, readily reach a prescribed value even by adsorption of a small amount of gases, thus presenting difficulties in determining whether the gases which happen to be present have such large volumes as would result from an accident or small volumes harmless to the human body which generally occur in the normal use of a gas implement. Therefore, any of the prior art gas-sensing materials have been found difficult of practical application. Further defects of the known gas-sensing materials are that they fail to distinguish between liquefied petroleum gases such as propane gas and butane gas on one hand and hydrogen gas or carbon monoxide gas on the other, and moreover readily indicate electric resistance changes even by a reducing type of gas like tobacco smoke.

It is accordingly an object of this invention to provide a gas-sensing material which is free from the above-mentioned shortcomings of the known gas-sensing materials and can indicate prominent changes in electric resistance in good linearity.

Another object of the invention is to provide a gas-sensing material which presents electric resistance changes in different degrees according to the kinds of gas to which the material is exposed.

Namely, this invention provides a gas-sensing material characteristically formed of a sinter containing 20 to 99.85 mol % of ZnO, 0.1 to 50 mol % of MgO and 0.05 to 30 mol % of $Me_2O_3$ (Me represents at least one element selected from the group consisting of gallium (Ga), boron (B), indium (In), iron (Fe), aluminium (Al) and chromium (Cr)).

According to another aspect of the invention, there is provided a gas-sensing material consisting of another sinter containing 0.01 to 10% by weight of platinum (Pt) based on the total amount of the above-mentioned three basic components of ZnO, MgO and $Me_2O_3$.

This invention can be more fully understood from the following detailed description when taken in conjunction with the accompanying drawings, in which.

Figure 3:
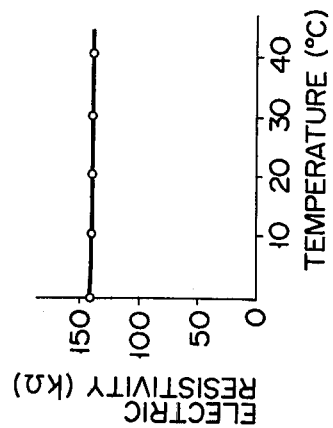
FIGS. 3 and 4 are curve diagrams showing the temperature characteristic of the gas-sensing material of the invention.

A gas-sensing material according to this invention is sinter formed of three basic components, that is, ZnO, MgO and $Me_2O_3$ (Me denotes at least one element selected from the group consisting of gallium, boron, indium, iron, aluminium and chromium). According to the invention, the properties of a gas-sensing material can be improved by blending a prescribed amount of platinum with the above-mentioned basic ternary system.

With this invention, the proportion of ZnO is chosen to range from 20 to 99.85 mol %, the proportion of MgO from 0.1 to 50 mol % and the proportion of $Me_2O_3$ from 0.05 to 30 mol % or preferably from 1 to 15 mol %. There will now be given the reason why these limitations are imposed on the contents of the three basic components of ZnO, MgO and $Me_2O_3$. For example, where ZnO has a larger proportion than 99.85 mol %, and MgO has a smaller proportion than 0.1 mol % or $Me_2O_3$ has a smaller proportion than 0.05 mol %, then the resultant gas-sensing material shows very small electric resistance changes in the adsorption and desorption of gases, undesirably presenting difficulties in detecting said changes. Where, therefore, the gas-sensing material is desired to indicate sufficiently large electric resistance changes, the proportion of $Me_2O_3$ should be at least 1 mol %. On the other hand, where ZnO has a smaller proportion than 20 mol % and MgO has a larger proportion than 50 mol % or $Me_2O_3$ has a larger proportion than 30 %, then the resultant gas-sensing material shows a higher electric resistance than hundreds of $M\Omega$ units, causing the gas-sensing circuit to have an unduly low gas sensitivity, and leading to the decreased precision of gas detection.

$Me_2O_3$ included as one component in the gas-sensing material of this invention is at least one compound selected from the group consisting of $Ga_2O_3$, $B_2O_3$, $In_2O_3$, $Fe_2O_3$, $Al_2O_3$ and $Cr_2O_3$. If necessary, these $Me_2O_3$ compounds may be used in any combination. Further, said $Me_2O_3$ compounds have the effect of causing the gas-sensing material to indicate prominent electric resistance changes in good linearity. Particularly, $Fe_2O_3$ and $Cr_2O_3$ noticeably elevate the electric resistance changes of the gas-sensing material. $Ga_2O_3$ and $In_2O_3$ not only help to render electric resistance changes noticeable, but also provide a gas-sensing material of a low electric resistance, thus enabling a gas detector to produce a large detection output. $B_2O_3$ improves the sintering property of the gas-sensing material and also minimizes its deterioration with time. $Al_2O_3$ has the effect of enabling the gas-sensing material to show noticeable electric resistance changes and a low temperature coefficient.

According to this invention, platinum is added to the basic ternary system consisting of ZnO, MgO and $Me_2O_3$ in an amount of 0.01 to 10% by weight. Platinum allows the gas-sensing material to present prominently different degrees of sensitivity according to the kinds of gas to which the material is exposed. For example, with aliphatic hydrocarbon gases, the larger the number of carbon atoms contained therein, the higher the sensitivity of a gas-sensing material containing platinum. In addition, platinum enables the gas-sensing material to show electric resistance changes in good linearity. However, a smaller proportion of platinum than 0.01 % by weight fails to attain the above-mentioned prominent effects, while a larger proportion of platinum than 10 % by weight leads to the more decreased electric resistance changes of the gas-sensing material and moreover causes said material to have a larger temperature coefficient relative to electric resistance, thus rendering said material less adapted for practical application. Viewed this way, the proportion of platinum is preferred to fall within the range of 0.1 to 1.0 % by weight based on the total amount of the aforesaid three basic components of ZnO, MgO and $Me_2O_3$.

Figure 1:
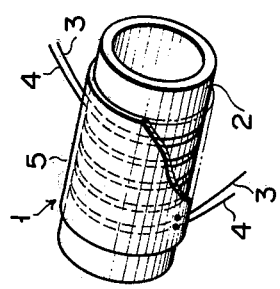
FIG. 1 is an oblique view, partly exploded, of a gas-sensing element using a gas-sensing material according to this invention.

These three basic components of ZnO, MgO and $Me_2O_3$ (Me represents at least one element selected from the group consisting of Ga, B, In, Fe, Al and Cr) may be used not only as pure compounds, but also other various forms of compounds that will change into these prescribed oxides upon heating, for example, as hydroxides, carbonates, oxalates and nitrate. Also, platinum may be used not only as a single metallic element but also in the form of compounds, such as $H_2PtCl\cdot H_2O$, $NH_4PtCl_6$, $K_2PtCl_4$, $K_2PtCl_6$ and $Na_2PtCl$.

Where a gas-sensing sinter is prepared, ZnO, MgO and $Me_2O_3$ (Me denotes at least one element selected from the group consisting of Ga, B, In, Fe, Al and Cr) and, if necessary, Pt are first weighed out in proper proportions jointly to form a prescribed composition. These materials are thoroughly mixed, for example, in a ball mill into powders whose particle sizes are well controlled and then kneaded into a past with addition of water or binder. The paste is coated over the peripheral surface of a cylindrical insulation substrate 2 included in a gas-sensing element 1 illustrated in FIG. 1. Prior to said coating, the peripheral surface of said cylindrical insulation substrate 2 is wound several times with two substantially parallel metal wires. After dried, the paste is baked into a gas-sensing sinter 5, for example, in the air by being heated at a proper level of temperature ranging from 600° to 800° C. Said baking may be effected either in an electric furnace or by introducing electric current through one of the electrodes 3, 4 acting as a heater.

A gas-sensing element 1 fitted with the gas-sensing material 5 determines the presence of gases from electric resistance changes occurring across the metal wires 3, 4 which correspond to the electric resistance changes of the gas-sensing material 5 resulting from the adsorption and desorption of gases. Namely, when a gas is adsorbed to the surface of the gas-sensing material 5, said material is reduced in electric resistance, giving rise to changes in the electric resistance across the electrodes 3, 4. Said electric resistance change forms a gas-detecting output, which in turn actuates a gas detector. In this case, one of the metal wires 3, 4 is heated to act as a heater so as to facilitate the adsorption of gases to the gas-sensing material 5 and the desorption of gases therefrom.

Figure 2:
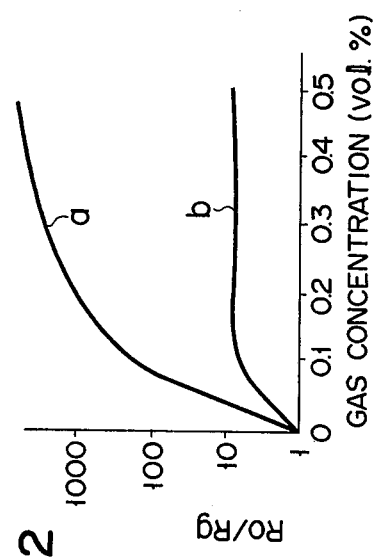
FIG. 2 is a curve diagram showing comparison between the ratio ($R_o/R_g$) of electric resistance exhibited by the gas-sensing material of the invention relative to gas concentrations and that of the prior art gas-sensing material.

When used with a gas-sensing element 1, the gas-sensing material of this invention displays the following properties. The gas-sensing material of the invention composed of ZnO, MgO, $Me_2O_3$ and Pt indicates electric resistance changes or sensitivities to gas concentrations, as shown by the curve $a$ in FIG. 2. Plotted on the ordinate of FIG. 2 is the ratio $R_o/R_g$ between the referential electric resistance $R_o$ of the gas-sensing material when it is not exposed to any gas and the electric resistance $R_g$ thereof when exposed to $C_4H_{10}$ gas. The concentrations or percentage volumes of said $C_4H_{10}$ gas are plotted on the abscissa. With the gas-sensing element 1 of this invention, the electric resistance ratio $R_o/R_g$ does not become fixed, but changes almost linearly when the concentrations of said $C_4H_{10}$ gas widely vary. Conversely in the case of the prior art $SnO_2$ type gas-sensing material shown in FIG. 2 for comparison, the electric resistance changes are smaller, as shown by the curve $b$, than in the gas-sensing material of this invention, namely, said electric resistance changes readily reach a maximum level even when the prior art gas-sensing material is exposed to the $C_4H_{10}$, as having a concentration of about 0.1 % by volume.

Further, experiments were made at room temperature of 25° C to determine the electric resistive changes of the gas-sensing material of this invention by varying the proportions of ZnO, MgO, $Me_2O_3$ and Pt within the ranges of 100 to 16 mol % for ZnO, 0 to 52 mol % for MgO, 0 to 32 mol % for $Me_2O_3$ and 0 to 15% by weight for Pt, the results being set forth in the following Tables.

Table 1

|  | ZnO (mol %) | MgO (mol %) | $Me_2O_3$ (mol %) | | $R_o$ (gas concentration %) | $R_o$ (gas concentration %) / $R_g$ (gas concentration %) |
|---|---|---|---|---|---|---|
| Control 1 | 100 | 0 | 0 | | 89 MΩ | 1.8 |
| Example 1 | 99.85 | 0.1 | Me : Ga | 0.05 | 14 " | $1 \times 10^2$ |
| 2 | " | " | " B | " | 65 " | $5 \times 10^2$ |
| 3 | " | " | " In | " | 23 " | $3 \times 10^2$ |
| 4 | 99.85 | 0.1 | " Fe | 0.05 | 16 " | $0.7 \times 10^2$ |
| 5 | " | " | " Al | " | 8 " | $0.8 \times 10^2$ |
| 6 | " | " | " Cr | " | 27 " | $1.1 \times 10^2$ |
| 7 | 99.75 | 0.1 | " { Ga In B | 0.05 " " | 7 " | $5 \times 10^3$ |
| 8 | 99.75 | 0.1 | " { Fe Al Cr | " " " | 9 " | $0.9 \times 10^3$ |
| 9 | 94.0 | 5.0 | " Ga | 1.0 | 800 KΩ | $6 \times 10^3$ |
| 10 | " | " | " B | " | 1200 " | $4 \times 10^3$ |
| 11 | " | " | " In | " | 560 " | $3 \times 10^3$ |
| 12 | 94.0 | 5.0 | " Fe | 1.0 | 950 " | $2 \times 10^3$ |
| 13 | " | " | " Al | " | 450 " | $1 \times 10^3$ |
| 14 | " | " | " Cr | " | 1270 " | $2 \times 10^3$ |
| 15 | 85.0 | 10.0 | " Ga | 5 | 620 " | $1 \times 10^4$ |
| 16 | " | " | " In | 5 | 540 " | $8 \times 10^3$ |

Table 1-continued

| | | ZnO (mol %) | MgO (mol %) | Me$_2$O$_3$ (mol %) | | | $R_o$ (gas concentration %) | $\frac{R_o \text{ (gas concentration \%)}}{R_g \text{ (gas concentration \%)}}$ |
|---|---|---|---|---|---|---|---|---|
| | 17 | " | " | " | B | 5 | 800 " | 2 × 10$^3$ |
| | 18 | 85.0 | 10.0 | " | Fe | 5.0 | 700 " | 1 × 10$^3$ |
| | 19 | 85.0 | " | " | Al | " | 550 " | 0.9 × 10$^3$ |
| | 20 | " | " | " | Cr | " | 1300 " | 1.5 × 10$^3$ |
| | 21 | 85.0 | 10.0 | " | In 3<br>Fe 5<br>Ga 2 | | 600 " | 2.6 × 10$^2$ |
| Example | 22 | 70 | 20 | Me: | B "<br>In "<br>Fe "<br>Al "<br>Ga 2 | | 190 KΩ | 5 × 10$^2$ |
| | 23 | 70 | 20 | " | B "<br>In "<br>Fe "<br>Cr " | | 240 " | 7 × 10$^2$ |
| | 24 | 70 | 20 | " | Ga | 10 | 140 " | 2 × 10$^3$ |
| | 25 | " | " | " | In | " | 130 " | 9 × 10$^2$ |
| | 26 | " | " | " | B | " | 430 " | 3 × 10$^2$ |
| | 27 | 70 | 20 | " | Fe | 10 | 420 " | 7 × 10$^2$ |
| | 28 | " | " | " | Al | " | 210 " | 3 × 10$^2$ |
| | 29 | " | " | " | Cr | " | 570 " | 6 × 10$^2$ |
| | 30 | 71 | " | " | Ga 3<br>In 3<br>B 3 | | 160 " | 4 × 10$^2$ |
| | 31 | 71 | 20 | " | Fe 3<br>Al 3 | | 250 " | 5 × 10$^2$ |
| | 32 | 71 | 20 | " | Cr " | | 250 " | 5 × 10$^2$ |
| | 33 | 55 | 30 | " | Ga | 15 | 400 " | 5 × 10$^2$ |
| | 34 | " | " | " | In | 15 | 290 " | 3 × 10$^2$ |
| | 35 | " | " | " | B | 15 | 820 " | 2 × 10$^2$ |
| | 36 | " | " | " | Ga 5<br>In 5<br>B 5 | | 3 MΩ | 3 × 10$^2$ |
| Example | 37 | 55 | 30 | Me: | Fe | 15 | 810 KΩ | 2 × 10$^2$ |
| | 38 | " | " | " | Al | " | 340 " | 1 × 10$^2$ |
| | 39 | " | " | " | Cr | " | 1100 " | 1 × 10$^2$ |
| | 40 | " | " | " | Fe 5<br>Al "<br>Cr " | | 740 " | 2 × 10$^2$ |
| | 41 | 40 | 40 | " | Ga | 20 | 76 MΩ | 2 × 10$^2$ |
| | 42 | " | " | " | In | " | 52 " | 1 × 10$^2$ |
| | 43 | " | " | " | B | " | 130 " | 1 × 10$^2$ |
| | 44 | " | " | " | Fe | 20 | 38 " | 0.7 × 10$^2$ |
| | 45 | " | " | " | Al | " | 10 " | 0.5 × 10$^2$ |
| | 46 | " | " | " | Cr | " | 45 " | 0.9 × 10$^2$ |
| | 47 | " | " | " | Ga 10<br>Al 10<br>B 10 | | 30 " | 1.3 × 10$^2$ |
| | 48 | " | " | " | Cr 10 | | 65 " | 1 × 10$^2$ |
| | 49 | 20 | 50 | " | Ga | 30 | 40 " | 1 × 10$^2$ |
| | 50 | " | " | " | In | 30 | 30 " | 80 |
| | 51 | " | " | " | B | 30 | 80 " | 50 |
| | 52 | " | " | " | Ga 10<br>In 10<br>B 10 | | 85 " | 80 |
| | 53 | 20 | 50 | " | Fe | 30 | 52 " | 3 × 10 |
| | 54 | " | " | " | Al | " | 15 " | 1 × 10 |
| | 55 | " | " | " | Cr | " | 60 " | 2 × 10 |
| | 56 | " | " | " | Fe 10<br>Al 10<br>Cr " | | 28 " | 3 × 10 |
| Control | 2 | 18 | 52 | Me: | Ga | 30 | 250 MΩ | 1.2 |
| | 3 | " | 50 | " | In | 32 | 120 " | 1.8 |
| | 4 | 16 | 52 | " | Fe | 32 | 75 " | 3.5 |

Table 2

| | ZnO (mol %) | MgO (mol %) | Me$_2$O$_3$ (mol %) | | Pt (wt. %) | $R_o$ (gas concentration %) | $\frac{R_o \text{ (gas concentration \%)}}{R_g \text{ (gas concentration \%)}}$ |
|---|---|---|---|---|---|---|---|
| Example 57 | 99.85 | 0.1 | Me = | Ga 0.05 | 0.01 | 24 MΩ | 14 × 10 |
| 58 | " | " | " = | B " | " | 85 " | 2.1 × 10 |
| 59 | " | " | " = | In " | " | 33 " | 1.8 × 10 |
| 60 | " | " | " = | Fe " | " | 28 " | 2.5 × 10 |
| 61 | " | " | " = | Al " | " | 17 " | 1.5 × 10 |
| 62 | " | " | " = | Cr " | " | 35 " | 2.0 × 10 |
| 63 | 98.9 | 1.0 | " = | Ga 0.1 | 0.05 | 19 " | 2.8 × 10 |
| 64 | " | " | " = | B " | " | 74 " | 4.2 × 10 |
| 65 | " | " | " = | In " | " | 28 " | 3.6 × 10 |
| 66 | " | " | " = | Fe " | " | 23 " | 4.9 × 10 |
| 67 | " | " | " = | Al " | " | 12 " | 3.1 × 10 |

Table 2-continued

| | ZnO (mol %) | MgO (mol %) | Me₂O₃ (mol %) | | | Pt (wt. %) | $R_o$ (gas concentration %) | $R_o$ (gas concentration %) / $R_g$ (gas concentration %) |
|---|---|---|---|---|---|---|---|---|
| 68 | " | " | " = | Cr | " | " | 29 " | $4.2 \times 10$ |
| 69 | 93 | 5.0 | " = | Ga | 2.0 | 0.01 | 1.2 " | $0.7 \times 10^2$ |
| 70 | " | " | " = | B | 2.0 | 0.10 | 4.2 " | $1.1 \times 10^2$ |
| 71 | " | " | " = | In | " | " | 1.6 " | $0.9 \times 10^2$ |
| 72 | " | " | " = | Fe | " | " | 1.1 " | $1.3 \times 10^2$ |
| 73 | " | " | " = | Al | " | " | 0.8 " | $0.6 \times 10^2$ |
| 74 | " | " | " = | Cr | " | " | 1.8 " | $1.0 \times 10^2$ |
| 75 | " | " | Me = { Ga 1.0, B ", Ga 1.0 } | | | 0.3 | 2.5 | $1.0 \times 10^2$ |
| Example 76 | 93 | 5.0 | Me = { Fe ", Ga " } | | | 0.5 | 1.2 MΩ | $1.1 \times 10^2$ |
| 77 | " | " | " = { Cr " } | | | " | 1.3 MΩ | $0.9 \times 10^2$ |
| 78 | 85 | 10 | " = | Ga | 5.0 | " | 820 KΩ | $1.5 \times 10^2$ |
| 79 | " | " | " = | B | " | " | 980 " | $2.4 \times 10^2$ |
| 80 | " | " | " = | In | " | " | 740 " | $2.7 \times 10^2$ |
| 81 | " | " | " = | Fe | " | " | 680 " | $2.7 \times 10^2$ |
| 82 | " | " | " = | Al | " | " | 400 " | $1.9 \times 10^2$ |
| 83 | " | " | " = | Cr | " | " | 720 " | $2.3 \times 10^2$ |
| 84 | " | " | " = { Ga 3, B 2, In 3 } | | | " | 920 " | $1.9 \times 10^2$ |
| 85 | " | " | " = { Fe 2, Al 3 } | | | " | 1000 " | $2.1 \times 10^2$ |
| 86 | " | " | " = { Cr 2 } | | | " | 980 " | $2.0 \times 10^2$ |
| 87 | 70 | 20 | " = | Ga | 10 | " | 540 " | $1.2 \times 10^2$ |
| 88 | " | " | " = | B | " | " | 930 " | $2.1 \times 10^2$ |
| 89 | " | " | " = | In | " | " | 430 " | $1.7 \times 10^2$ |
| 90 | " | " | " = | Fe | " | " | 310 " | $2.3 \times 10^2$ |
| 91 | " | " | " = | Al | " | " | 190 " | $1.5 \times 10^2$ |
| 92 | " | " | " = | Cr | " | " | 380 " | $1.9 \times 10^2$ |
| 93 | " | " | " = { Ga 2, B ", In ", Fe ", Al " } | | | 1.0 | 850 " | $1.5 \times 10^2$ |
| 94 | " | " | " = { Ga ", B ", In ", Fe ", Cr " } | | | " | 940 " | $1.8 \times 10^2$ |
| Example 95 | 50 | 30 | Me = | Ga | 20 | 5.0 | 1.1 MΩ | $0.7 \times 10^2$ |
| 96 | " | " | " = | B | " | 5.0 | 1.9 " | $1.1 \times 10^2$ |
| 97 | " | " | " = | In | " | " | 0.9 " | $0.8 \times 10^2$ |
| 98 | " | " | " = | Fe | " | " | 0.8 " | $0.9 \times 10^2$ |
| 99 | " | " | " = | Al | " | " | 0.5 " | $0.8 \times 10^2$ |
| 100 | " | " | " = | Cr | " | " | 0.7 " | $1.0 \times 10^2$ |
| 101 | " | " | = { Ga 5, B ", In ", Fe " } | | | " | 1.5 " | $1.0 \times 10^2$ |
| 102 | " | " | = { Ga ", B ", Al ", Cr " } | | | " | 1.2 " | $0.9 \times 10^2$ |
| 103 | 40 | 40 | " = { Ga 10, B " } | | | 10 | 13 " | $4 \times 10$ |
| 104 | " | " | " = { Ga 10, Al ", B " } | | | " | 8 " | $6 \times 10$ |
| 105 | " | " | " = { Cr ", Ga " } | | | " | 15 " | $7 \times 10$ |
| 106 | 20 | 50 | " = { B ", Al ", Ga " } | | | " | 32 " | $2.5 \times 10$ |
| 107 | " | " | " = { B ", Cr " } | | | " | 29 " | $2.8 \times 10$ |
| 108 | " | " | " = { Ga 5, B ", In ", Fe ", Al ", Cr " } | | | " | 35 " | $1.9 \times 10$ |
| Control 5 | 16 | 52 | Me = | Cr | 32 | 15 | 76 MΩ | 3.1 |

In the above tables, the gas sensitivities of a gas-sensing material are expressed in the ratio of $R_o/R_g$ between the electric resistance $R_o$ of said material when the $C_4H_{10}$ gas has a concentration of 0% and the electric resistance $R_g$ of said material when the $C_4H_{10}$ gas has a concentration of 0.1 % by volume.

Figure 4:
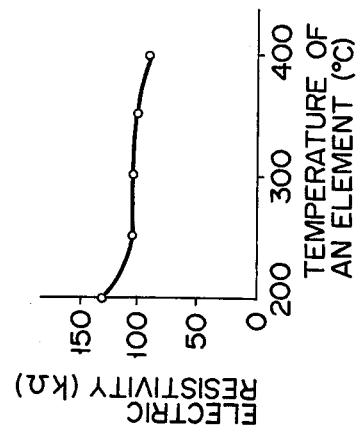

Determination was also made of the temperature characteristic of the gas-sensing material of this invention, the results being set forth in FIGS. 3 and 4. While the results were based on Example 27, the same temperature characteristic was confirmed with respect to the other examples. FIG. 3 shows the electric resistance changes of the subject gas-sensing material resulting from variations in ambient temperature FIG. 4 indicates the electric resistance changes of said gas-sensing material caused by variations in the temperature of heat applied by the heater. In both cases, the gas-sensing material presents prominent stability.

Figure 5:
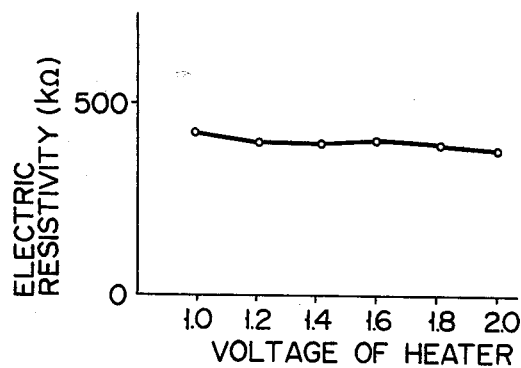
FIG. 5 is a curve diagram showing the electric resistance changes of the gas-sensing material of the invention relative to heater voltage.

When used with a gas-sensing element provided with a heater, the gas-sensing material of this invention presented only small electric resistance changes, as shown in FIG. 5, relative to variations in the voltage of said heater, namely, was confirmed to have good stability.

Figure 6:
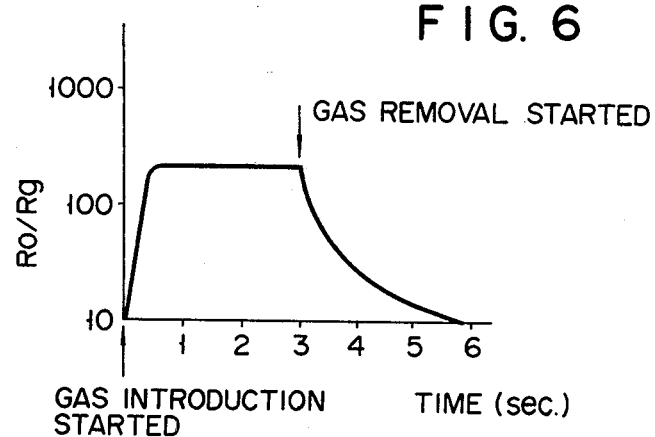
FIG. 6 shows the response characteristic of the gas-sensing material of the invention relative to its exposure to gases or its removal therefrom.

The gas-sensing material of this invention was proved to have such sensitive response to gases that, as indicated in FIG. 6, the electric resistance of said gas-sensing material was lowered to a prescribed level within 1 second after exposure to gases and restored to the original level corresponding to a gas-free condition within several seconds after gases were removed. FIG. 6 illustrates the response characteristic of the gas-sensing material of this invention when exposed to 0.1 % by volume of $C_4H_{10}$ gas.

Figure 7:
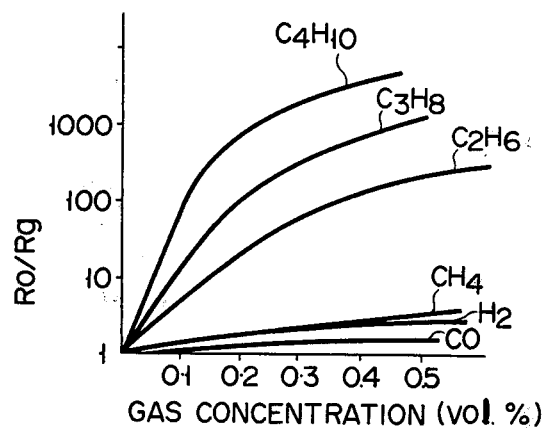
FIG. 7 is a curve diagram showing the different degrees of sensitivity of the gas-sensing material of the invention to the various kinds of gas to which said material is exposed.

Further, the gas-sensing material of the invention which indicates different degrees of sensitivity of various kinds of reducing gas can effectively distinguish between them. FIG. 7 shows the results of determining the different degrees of gas sensitivity exhibited by the gas-sensing sinter of this invention which consists of the three basic components of ZnO, MgO and $Me_2O_3$ blended with a specified amount of Pt. As apparent from FIG. 7, the subject gas-sensing material presents a higher sensitivity to gases, as they contain a larger number of carbon atoms. Therefore, the gas-sensing material of this invention is well adapted for use with an analytic apparatus designed to determine the composition of a gaseous mass.

What we claim is:

1. A gas-sensing material which comprises a sinter consisting essentially of 20 to 99.85 mol % of ZnO, 0.1 to 50 mol % of MgO and 0.05 to 30 mol % of $Me_2O_3$ wherein, Me is at least one element selected from the group consisting of gallium, boron, indium, iron, aluminum and chromium.

2. The gas-sensing material according to claim 1, wherein the proportion of the $Me_2O_3$ component is chosen to range from 1 to 15 mol %.

3. The gas-sensing material according to claim 1, wherein $Me_2O_3$ is at least one compound selected from the group consisting of $Fe_2O_3$ and $Cr_2O_3$.

4. The gas-sensing material according to claim 1, wherein $Me_2O_3$ is at least one compound selected from the group consisting of $Ga_2O_3$ and $In_2O_3$.

5. The gas-sensing material according to claim 1, wherein $Me_2O_3$ is at least $B_2O_3$.

6. The gas-sensing material according to claim 1, wherein $Me_2O_3$ is at least $Al_2O_3$.

7. A gas-sensing material which comprises a sinter consisting essentially of 20 to 99.85 mol % of ZnO, 0.1 to 50 mol % of MgO, 0.05 to 30 mol % of $Me_2O_3$, wherein Me is at least one element selected from the group consisting of gallium, boron, indium, iron, aluminum and chromium, and from 0.01 to 10 weight % of platinum based on the total amount of said ZnO, MgO and $Me_2O_3$.

8. The gas-sensing material according to claim 7, which contains 0.1 to 1% by weight of platinum.

* * * * *